(12) United States Patent
Heroux et al.

(10) Patent No.: US 8,074,465 B2
(45) Date of Patent: Dec. 13, 2011

(54) THERMALLY INSULATED TRANSPORT CONTAINER FOR CELL-BASED PRODUCTS AND RELATED METHODS

(75) Inventors: Adam Heroux, Lowell, MA (US); Barbara Seymour, Natick, MA (US)

(73) Assignee: Genzyme Corporation, Cambridge, MA (US)

(*) Notice: Subject to any disclaimer, the term of this patent is extended or adjusted under 35 U.S.C. 154(b) by 945 days.

(21) Appl. No.: 12/066,454

(22) PCT Filed: Sep. 11, 2006

(86) PCT No.: PCT/US2006/035242
§ 371 (c)(1),
(2), (4) Date: Mar. 11, 2008

(87) PCT Pub. No.: WO2007/033051
PCT Pub. Date: Mar. 22, 2007

(65) Prior Publication Data
US 2008/0276643 A1    Nov. 13, 2008

Related U.S. Application Data

(60) Provisional application No. 60/716,257, filed on Sep. 12, 2005.

(51) Int. Cl.
*F25D 3/08* (2006.01)
(52) U.S. Cl. .............................. 62/371; 62/457.2; 62/530
(58) Field of Classification Search .................... 62/371, 62/372, 457.2, 457.5, 530
See application file for complete search history.

(56) References Cited

U.S. PATENT DOCUMENTS 2,724,494 A * 11/1955 Graff .......................... 206/545
5,435,142 A *  7/1995 Silber ............................. 62/60

* cited by examiner

*Primary Examiner* — Melvin Jones
(74) *Attorney, Agent, or Firm* — Finnegan, Henderson, Farabow, Garrett & Dunner, LLP

(57) ABSTRACT

The present invention provides a temperature sensitive transport container (20) for packaging and shipping cell-based products such as cultured cells intended for transplantation. In particular, the present disclosure provides a thermally insulated transport container system (10) for storing and transporting cells for transplantation which is capable of maintaining the cells at a desirable temperature range for a sufficient period of time to ensure adequate cell viability and therapeutic properties.

56 Claims, 7 Drawing Sheets

THERMALLY INSULATED TRANSPORT CONTAINER FOR CELL-BASED PRODUCTS AND RELATED METHODS

This application claims priority to U.S. provisional patent application No. 60/716,257, filed on Sep. 12, 2005, incorporated herein by reference in its entirety.

FIELD OF THE INVENTION

The present invention relates to temperature-sensitive packaging for use in the biotechnological and medical industries. In particular, the present invention relates to a thermally insulated container system for shipping cells. Even more particularly, the present invention relates to a thermally insulated container system for storing and transporting cells for transplantation which is capable of maintaining the cells at a desirable temperature range for a specified period of time.

BACKGROUND OF THE INVENTION

Current advances in biotechnology have introduced a variety of new therapeutic products to the market. Nowhere is this more true than in the medical industry. Instead of traditional drugs taken orally or intravenously, many of the new therapies involve the delivery of biological or cellular products directly to the patient. For example, cellular transplantation has recently emerged as a potential new treatment for many diseases or physical defects due to injury that could result in the loss of specialized cells within organ systems, eventually leading to organ system failure. The potential to treat these conditions with cell-based therapies holds promise for tissue/organ repair with the ultimate goal to regenerate and restore normal function.

The field of regenerative biology as it applies to regenerative medicine is an increasingly expanding area of research with hopes of providing therapeutic treatments for diseases and/or injuries that conventional medicines and even new biologic drug therapies cannot effectively treat. Extensive research in the area of regenerative medicine is focused on the development of cells, tissues and organs for the purpose of restoring function through transplantation. Replacement, repair and restoration of function is best accomplished by cells, tissues or organs that can perform the appropriate physiologic/metabolic duties. Several strategies are currently being investigated and include cell therapies derived from a variety of stem cells, including bone marrow, mesenchymal stem cells, cord blood stem cells, embryonic stem cells, as well as cells, tissues and organs from genetically modified animals.

A number of pre-clinical models as well as clinical applications involving cell therapy currently exist or are being explored. For example, cell therapies have been used to rebuild damaged cartilage in joints, repair spinal cord injuries, strengthen a weakened immune system, treat autoimmune diseases such as AIDS, and help patients with neurological disorders such as Alzheimer's disease, Parkinson's disease, and epilepsy. Further uses have included the treatment of a wide range of chronic conditions such as arteriosclerosis, congenital defects, and sexual dysfunction. Cell therapy has also been explored as a cancer treatment.

Another application of autologous cell transplantation involves the use of cell therapy to treat heart tissue damaged by myocardial infarction (MI). In one particular application, myoblasts harvested from a muscle biopsy can be transplanted as an adjunct to coronary artery bypass surgery, such as for example, by injecting the myoblast cells directly into a scarred or damaged heart, i.e., into the scar tissue or pre-infarct zone of damaged myocardium. Such a treatment technique would address acute injuries of the myocardium while also slowing or preventing the progression of congestive heart failure or scar formation.

With the clinical promise of novel therapeutic strategies comes new challenges. Because these cellular therapeutic products are living cells and delivered to the surgeon or care provider, it is desirable to understand not only how to reliably produce these products but also how to deliver them to the surgeon or care provider while preserving their viability and therapeutic properties. Accordingly, the need for temperature-sensitive packaging becomes critical as these cell therapies are brought to market. There is thus a need for storage and container systems that take into account the biological and physical requirements of transporting live cells, and in particular the effects of temperature constraints of the shipping process on the biological products. Specifically, there is a need for a storage and container system that can maintain the viability and therapeutic properties of the cells for a sufficient period of time during shipping or transport.

SUMMARY OF THE INVENTION

In accordance with the invention, the present disclosure provides a temperature sensitive transport container for packaging and shipping cell-based products such as living cells intended for transplantation. In particular, the present disclosure provides a thermally insulated transport container system for storing and transporting skeletal myoblast cells for transplantation which is capable of maintaining the cells at a desirable temperature range for a sufficient period of time to ensure adequate cell viability and therapeutic properties of the cells.

In an exemplary embodiment, the present disclosure provides a thermally insulated transport container system that includes a closable container having a thermally insulated portion, the container being configured for storage and shipment of a cell-based product. The system also includes a sealable canister within the container, the canister being configured for holding the cell-based product, and a refrigerant within the container, the refrigerant being configured to maintain an internal temperature of the canister in the range of $-5°$ C. to $15°$ C. for a period of at least 72 hours when the container has been closed. Preferably, the refrigerant is configured to maintain an internal temperature of the canister in the range of $-1°$ C. to $10°$ C. for a period of at least 72 hours, and more preferably, in the range of $-1°$ C. to $6°$ C. for a period of at least 72 hours.

In another exemplary embodiment, a method of shipping skeletal myoblast cells for transplantation is provided with the present disclosure. The method includes the step of providing a closable container having a thermally insulated portion, the container being configured for storage and shipment of a cell-based product, including but not limited to a skeletal myoblast cell-based product, providing the cells in a sealed canister configured for holding cell-based products, and placing the sealed canister into the container. A refrigerant is provided for the container, the refrigerant being configured to maintain an internal temperature of the canister in the range of $-5°$ C. to $15°$ C. for a period of at least 72 hours. Preferably, the refrigerant is configured to maintain an internal temperature of the canister in the range of $-1°$ C. to $10°$ C. for a period of at least 72 hours, and more preferably, in the range of $-1°$ C. to $6°$ C. for a period of at least 72 hours. The container is closed with the refrigerant arranged around the sealed canister and can be ready for shipping after the proper labels have been placed on the container.

In yet another exemplary embodiment, a method of transporting skeletal myoblast cells to a recipient is provided. The method includes the step of maintaining the skeletal myoblast cells at a temperature range of −1° C. to 6° C. during transportation, for a duration of at least 48 hours, preferably at least 72 hours, and more preferably at least 96 hours. The skeletal myoblast cells can be suspended in medium and configured for transplantation. The method also includes the step of delivering the skeletal myoblast cells to the recipient in therapeutically acceptable condition.

Additional objects and advantages of the invention will be set forth in part in the description which follows, and in part will be apparent from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate one embodiment of the invention and together with the description, serve to explain the principles of the invention.

DESCRIPTION OF THE EMBODIMENTS

Figure 1:
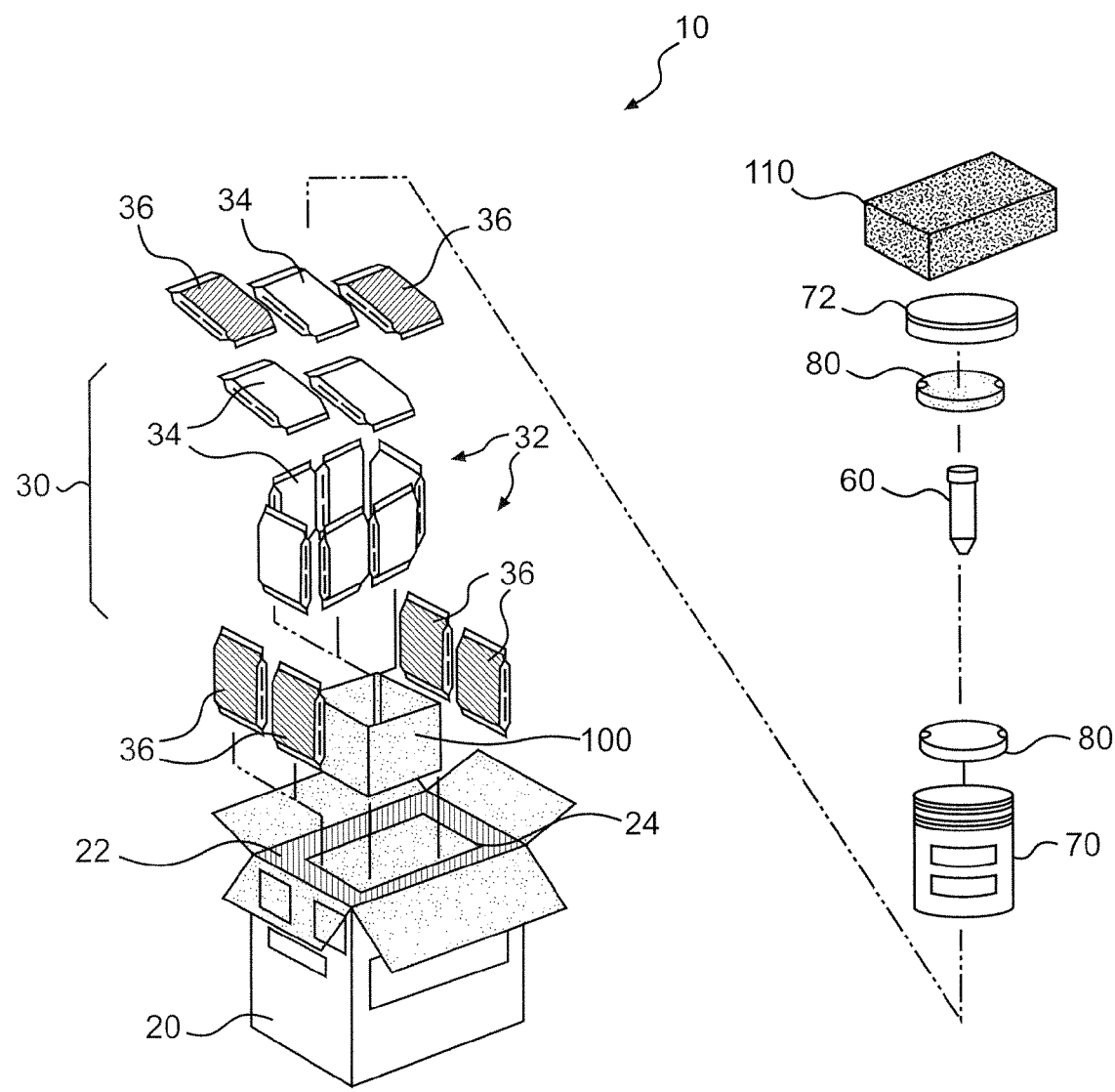
FIG. 1 is an exploded view of a transport container system in accordance with one exemplary embodiment of the present invention.

Reference will now be made in detail to the present embodiments (exemplary embodiments) of the invention, an example of which is illustrated in the accompanying drawings. Wherever possible, the same reference numbers will be used throughout the drawings to refer to the same or like parts.

The present disclosure provides a temperature sensitive transport container system for packaging and shipping cells useful for transplantation. Even more particularly, the present disclosure provides a thermally insulated transport container system for storing and transporting skeletal myoblast cells which is capable of maintaining the cells at a desirable temperature range for a sufficient period of time to ensure adequate cell viability and therapeutic properties of the cells.

The packaging and shipping container system of the present disclosure is designed to ensure tissue integrity and prevent contamination of the contents of the final containers holding the cell-based product. In addition, the container system takes into account the shelf life of the living product, where shelf life can be broadly defined as the measure of how long a product will maintain its viability and therapeutic properties at a given temperature. Temperature is one of the most critical elements for preserving the function of living cell-based products. These cell-based products will not survive as required if they are not specially prepared and protected for the rigors of the shipment process. In the case of cell-based products, and more particularly skeletal myoblast cell-based products, for transplantation the container system of the present disclosure guarantees the efficacy of the product by maintaining the desired temperature range for the duration of the shelf life of the cell-based products.

Further, the container system also takes into account the size and weight of the final package and to this end, provides a relatively small and lightweight packaging for convenient, efficient and economical transport of the cells. To maintain a narrow temperature range for an extended period of time, the amount of insulation and refrigerant required can be dramatic. The larger the temperature range allowed by the shelf life, the smaller and less insulation the package requires. These factors must be taken into account when identifying a carrier of the package, since commercial carriers charge by size and weight. If the package is going to be transported over ground, some variables to consider are whether the transportation is climate controlled, whether the package is being shipped in a shared cargo hold and, if not, whether the package will be given a direct route from the facility to the recipient.

Additionally, the requirements of all federal, state and local shipping regulations may need to be taken into account. These regulations include those established by, for example, the International Air Transportation Association (IATA), the United States Department of Transportation (DOT), and the Transportation Security Administration (TSA). For example, the container must meet Federal published guidelines of Title 49 of the Code of Federal Regulations (CFR) established by the DOT for shipping diagnostic or infectious substances when cultured cells or blood products are being shipped. These guidelines include how to label, pack and test the package.

Turning now to the drawings and in particular to FIG. 1, an exemplary transport container system 10 of the present disclosure is shown. The container system 10 includes an insulated shipping container 20 configured for transporting temperature-sensitive cell-based products therein. The shipping container 20 can be, for example, an extruded polystyrene cooler or, as shown, a corrugated cardboard box lined with an insulation material 22 which has an R-value greater than 4 per inch. Preferably, the insulation material 22 has an R-value greater than 5 per inch, more preferably an R-value greater than 6 per inch, and even more preferably an R-value greater than 7 per inch. The insulation material can be formed of a urethane, and preferably, a blown polyurethane. Other suitable insulation materials can include, for instance, fiberglass, and cellulose having a sufficiently high R-value to provide adequate insulation power and to resist heat transfer. A liner 24 formed of, for example, corrugated cardboard can surround the insulation material 22.

Inside the shipping container 20, a refrigerant 30 is provided to help cool the contents of the shipping container 20 during shipping. The refrigerant 30 can include, for example, dry and wet ice, silicate gel packs, and other phase transition temperature packs. These packs can be shaped as refrigerant bricks. As shown in FIG. 1, in one exemplary embodiment the refrigerant 30 can include an arrangement of cold packs, preferably silicate gel packs 32. These silicate gel packs 32 can be further classified as either refrigerated gel packs 34 or frozen gel packs 36. The refrigerated gel pack 34 should be of the type that can be refrigerated at a temperature range between 2° C. to 8° C. The frozen gel pack 36 should be of the type that can be frozen to about −20° C. For example, the frozen gel pack 36 can be of a type suitable for freezing, such as for example, the frozen gel pack manufactured by Tech Pak Solutions, Inc. under the trade name Frigid Ice™. Preferably, each of these gel packs 32 should be nontoxic and be made from a foodgrade formula (i.e., with ingredients included on the U.S. Food and Drug Administration's GRAS list as acceptable food additives).

The different types of refrigerant sources provide different thermal properties that affect the overall function of the package. By varying the type of refrigerant source and its location relative to the cell-based product, the desired temperature can be achieved within the packaging. The use of multiple temperature refrigerant sources creates convection within the package. The low temperature sources (which in the exemplary embodiment are the frozen gel packs 36) will act as heat sinks, and aid in buffering the cell-based product from the ambient temperature. The warmer refrigerant sources (in the exemplary embodiment, that would be the refrigerated gel packs 34) aid in buffering the cell-based product from becoming too cold, and prevent the product from dropping below the temperature range of its shelf life. Further, all of the refrigerant sources 30 add mass to the packaging and thereby dampens the effect of the ambient temperature on the temperature of the cell-based product being transported.

Figure 2:
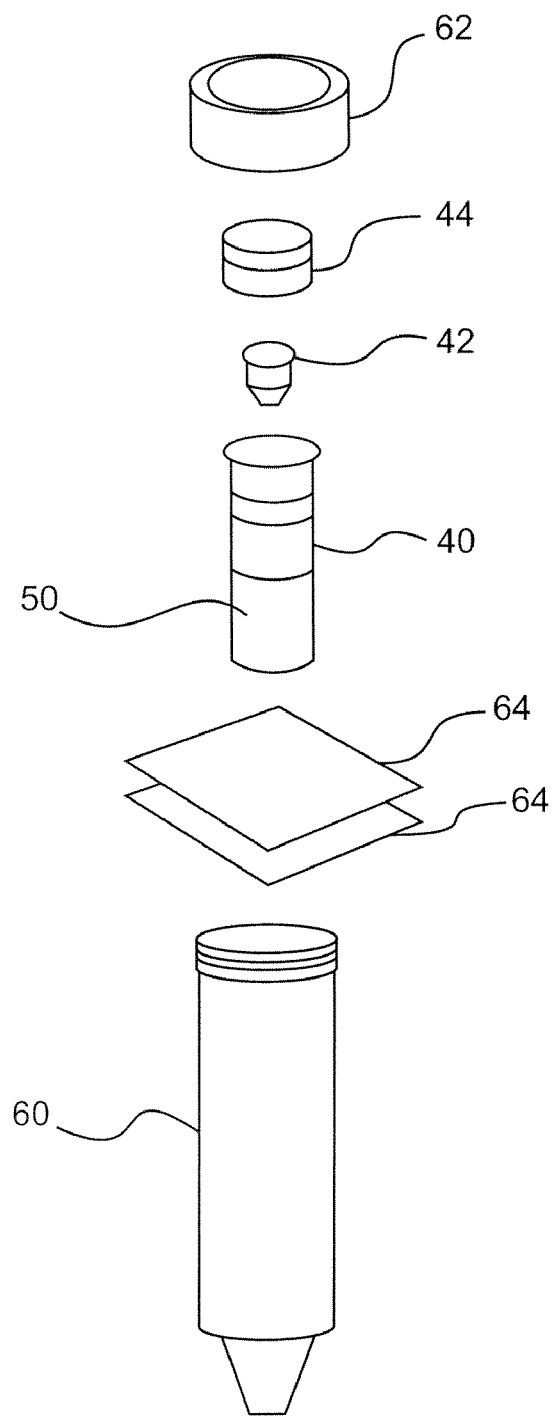
FIG. 2 is an exploded view of a final container usable with the container system of FIG. 1.

The transport container system 10 of the present disclosure can be used in one embodiment for storing and shipping cell-based products such as cultured cells 40, preferably skeletal myoblast cells, suspended in delivery medium for injection and/or transplantation. As shown in FIG. 2, the cell-based product 40 can be held in a container such as, for example, a sterile glass vial 50. A sterile stopper 42 can be placed onto the sterile vial 50 and a sterile crimp 44 placed over the stopper 42 and the opening of the vial 50 to securely close the vial 50. Preferably, the sterile stopper 42 can be a siliconized stopper and the sterile crimp 44 a flipoff-tearoff crimp. The vial 50 with the cell-based product 40 can be placed within another container, such as in tube 60 as shown. It is understood, however, that any suitable container may be used to hold the cultured cells, and that any suitably configured vial and stopper combination may be utilized without departing from the spirit of the invention.

In order to provide some cushion for the vial 50 as it is transported within the tube 60, sterile gauze sponges or mesh 64 can be placed in between the vial 50 and the tube 60. Of course, it is understood that a number of other materials can be used to cushion the vial 50, so long as it is sterile and has sufficient physical properties to dampen the external forces on the vial 50. A lid 62 is also provided for tightly closing the opening of the tube 60. The lid 62 may be, for example, a screw-top type or a snap-on type, depending on the type of tube 60 being used. Preferably, the tube 60 should be made from a sterilizable material. In the exemplary embodiment shown, the tube 60 can be, for example, a 50 mL centrifuge tube 60 having a screw-top lid 62.

The tube 60 containing the vial 50 with the cell-based product 40 therein can be placed inside an approved infectious substance shipping vessel or container such as a cylindrical shipping canister 70, as shown in FIG. 1, which meets national and international regulations for surface and air transportation of infectious substances. The canister 70 can include a screw-top lid 72 for sealing the contents of the canister 70 therein. Examples of shipping canisters 70 suitable for use with the present shipping system 10 can be of the type sold by Saf-T-Pak, Inc. (www.saftpak.com). Further, appropriate labels should be included to clearly identify the contents of the sealed shipping canister 70 and to provide warnings as necessary.

For the convenience of the surgeon or care provider, other related instruments may optionally be provided along with the cell-based product 40. These instruments can include, for example, syringes, needles, injection needle assemblies, and fluid transfer devices. Of course, these instruments are merely exemplary of the kinds of peripheral accessories or devices that may be included, and it is contemplated that other instruments may also be included depending on the nature and type of cell therapy involved.

Figure 3:
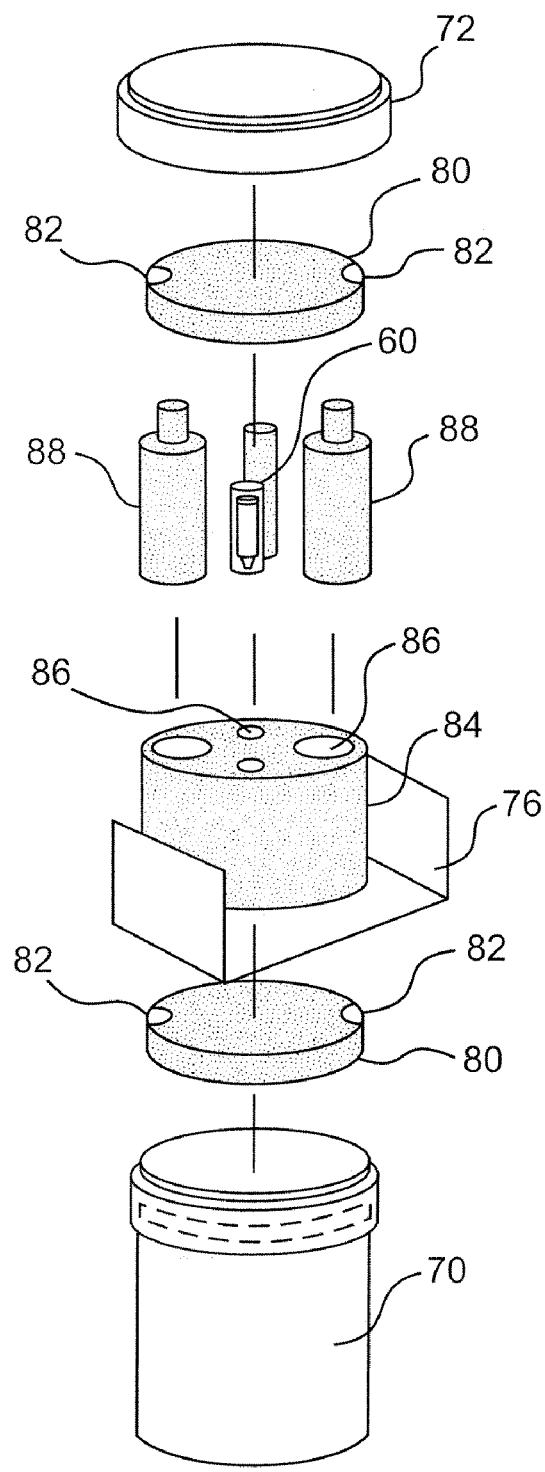
FIG. 3 is an exploded view of a shipping canister in accordance with an exemplary embodiment of the present invention.

Cushion inserts 80 can be placed inside the shipping canister 70 to prevent damage and/or breakage of the tube 60 during the shipping process. The cushion inserts 80 can preferably be formed from a foam material. As shown in FIG. 3, the cushion inserts 80 can be shaped like discs with notches 82 cut out from the sides to provide a convenient gripping surface for the handler's fingers. The inserts 80 are sized and configured to fit snugly inside the shipping canister 70 while still being easily removable. In the exemplary embodiment illustrated, a first cushion insert 80 is placed on the bottom of the shipping canister 70, while a second cushion insert 80 is placed at the top, just beneath the canister lid 72. It is understood, of course, that any number of cushion inserts 80 may be used in the present system 10, as deemed necessary and as available to the packager.

Optionally, additional cushion bodies may be provided to cushion the shipped items within the canister 70. For example, a cushion body 84 can be placed between the two cushion inserts 80, as shown in FIG. 3. The cylindrically shaped cushion body 84 includes differently sized plugs 88 which, when removed, provide the cushion body 84 with openings 86 for holding products to be shipped. The plugs 88 may be provided in varying size gradations which are concentrically nested, such that removal of a first plug provides one sized opening, while removal of a second, outer plug provides the cushion body 84 with a larger opening. As illustrated, tube 60 may be placed within an opening 86 of a cushion body 84 inside the sealed shipping canister 70. Collectively, the cushion inserts 80 and cushion body 84 provide a secure housing to help maintain the instruments and cell product(s) in a stable orientation during the shipping process. An absorbent sheet of material 76, such as for example, a fabric, mesh, gauze, or paper may be placed beneath the cylindrical body 84 as shown, in case of breakage and spillage of any liquids within the canister 70.

Once all of the products and instruments have been placed within the shipping canister 70, the sealed shipping canister 70 can then be placed within the shipping container 20 for transport. A divider 100 may be provided to create additional compartments for arranging the contents within the shipping container 20, and act as a divider between layers of the gel packs 32. The divider 100 can be formed from, for example, corrugated cardboard. The refrigerant 30 can then be arranged within the shipping container 20 and a foam plug 110 placed into the opening of the shipping container. Preferably, the foam plug 110 is configured to snugly and securely fit within the opening. The shipping container 20 can then be sealed and the appropriate labels placed thereon in preparation for transport.

The transport container system 10 of the present disclosure can be used for shipping a variety of different biological or cell-based products, and especially live cell products such as skeletal myoblast cells, that are temperature-sensitive (i.e., susceptible to temperature variations). In particular, the transport container system 10 provides an environment that can maintain the temperature of the product at a temperature range of −5° C. to 15° C., more preferably at a range of −1° C. to 10° C., and even more preferably at a range of −1° C. to 6° C. Preferably, the transport container system 10 can maintain the temperature of the cell-based product at the above-specified ranges for a period of at least 48 hours, more preferably 54 hours, even more preferably 60 hours, still more preferably 66 hours, even still more preferably 72 hours, and preferably still 96 hours, or even more preferably 120 hours or more. Such an environment would be suitable for live cell-based products having shelf life requirements within those temperature ranges and which are intended for delivery over the course of up to between 2 to 4 days prior to reaching the intended recipient. Further, such a system 10 would be suitable for shipping skeletal myoblast cells in particular, due to the sensitivity of these cells to temperature fluctuations, since such fluctuations can negatively affect their viability and therapeutic properties.

The above-described temperature ranges can be achieved during the shipping process due to the combination of the insulation properties of the shipping container 20 and the arrangement of the gel packs 32. As shown in FIG. 1, frozen gel packs 36 can be arranged as a layer outside the barrier or divider 100, and between the divider 100 and the insulated layer 22 of the shipping container 20. Refrigerated gel packs 34 can be arranged as a layer inside the divider 100, and surrounding the sealable shipping canister 70. A combination of the refrigerated gel packs 34 and frozen gel packs 36 can be placed in more than one layer on top of the opening. Preferably, a layer comprising refrigerated gel packs 34 is placed on top of the sealed shipping canister 70 and around the opening of the divider 100. Another layer including a combination of frozen gel packs 36 and refrigerated gel pack 34 is placed over the top of the collection of gel packs 32. Preferably, as shown in FIG. 1, the combination includes two frozen gel packs 36 and one refrigerated gel pack 34 arranged in alternating pattern (i.e., with the refrigerated gel pack 34 between the frozen gel packs 36).

As previously discussed, the different types of refrigerant sources provide different thermal properties that affect the overall function of the package. By varying the type of refrigerant source and its location relative to the product, the desired temperature ranges can be achieved within the packaging during the shipping process. This is because the use of multiple temperature refrigerant sources creates convection within the package. The frozen gel packs 36 act as heat sinks and aid in buffering the product from the ambient temperature, while the refrigerated gel packs 34 aid in buffering the product from becoming too cold, and prevent the product from dropping below the temperature range of its shelf life. Further, all of the cold or gel packs 32 add mass to the packaging and thereby dampen the effect of the ambient temperature on the temperature of the product being transported. Consequently, the arrangement or pattern of the different temperature gel packs 32, combined with the insulation properties of the shipping container 20, provide a transport container system 10 that can achieve these specific temperature ranges.

It is understood that the transport container system 10 of the present disclosure can be used for shipping a variety of different biological or cell-based products, and in particular living cell-based products that are susceptible to temperature variations. A number of cell-based products that could benefit from being shipped using the present transport container system 10 include, for example, autologous cultured chondrocytes, neural renal cells, and preferably, autologous or allogeneic skeletal myoblast cells, either culture or uncultured. Of course, it is contemplated that any living cell-based product having a shelf life consistent with the temperature ranges provided by this transport container system 10 would benefit from being shipped using the present system 10.

In the final cell product, the suspension or transport medium used should provide stability (i.e., sufficient viability and therapeutic properties) to the final cell-based product in connection with the transport container system 10 for at least 72 hours. For example, a suitable suspension medium would be one that would provide an acceptable shelf life specification of greater than 50% viability after 72 hours of storage and/or shipping at these temperature ranges. Preferably, the cell viability is greater than 70% and more preferably, greater than 80%, more preferably still greater than 85%, and even more preferably still greater than 90%.

One preferred suspension medium particularly useful for skeletal myoblast cell-based products is Dulbecco's Modified Eagle's Medium (DMEM), with high glucose containing L-glutamine and HEPES buffer, without sodium pyruvate and without Phenol Red, and with or without Human Serum Albumin (HSA) at a concentration of 0.1%. Such a medium is disclosed in U.S. patent application Ser. No. 10/314,257, the contents of which are hereby incorporated in its entirety by reference. Of course, it is contemplated that other suspension mediums and components can also be used. One skilled in the art will recognize, of course, that the suspension or transport medium used should be one that is well-suited for the specific cell-based product being shipped or transported, since it is known that cell viability of a particular cell type can be dependent upon the media used. For example, protein stabilizers other than HSA, such as Bovine Serum Albumin (BSA), may also be used. Another suitable suspension medium is HypoThermosol® (HTS-DCC) sold by BioLife Solutions, Inc., a cell-specific, hypothermic preservation media that can be optimally used at a temperature range of 4-10° C.

Validation Study

For cell-based products and/or tissue that require specific environmental conditions other than ambient temperature, the capability of the transport container to maintain the required environmental conditions can preferably be demonstrated and documented in a validation study. The length of time that these conditions can be maintained by the transport container, assuming normal handling, can preferably also be determined and documented. The expiration dates of the transport container may be noted on the outside of the container.

Figure 4:
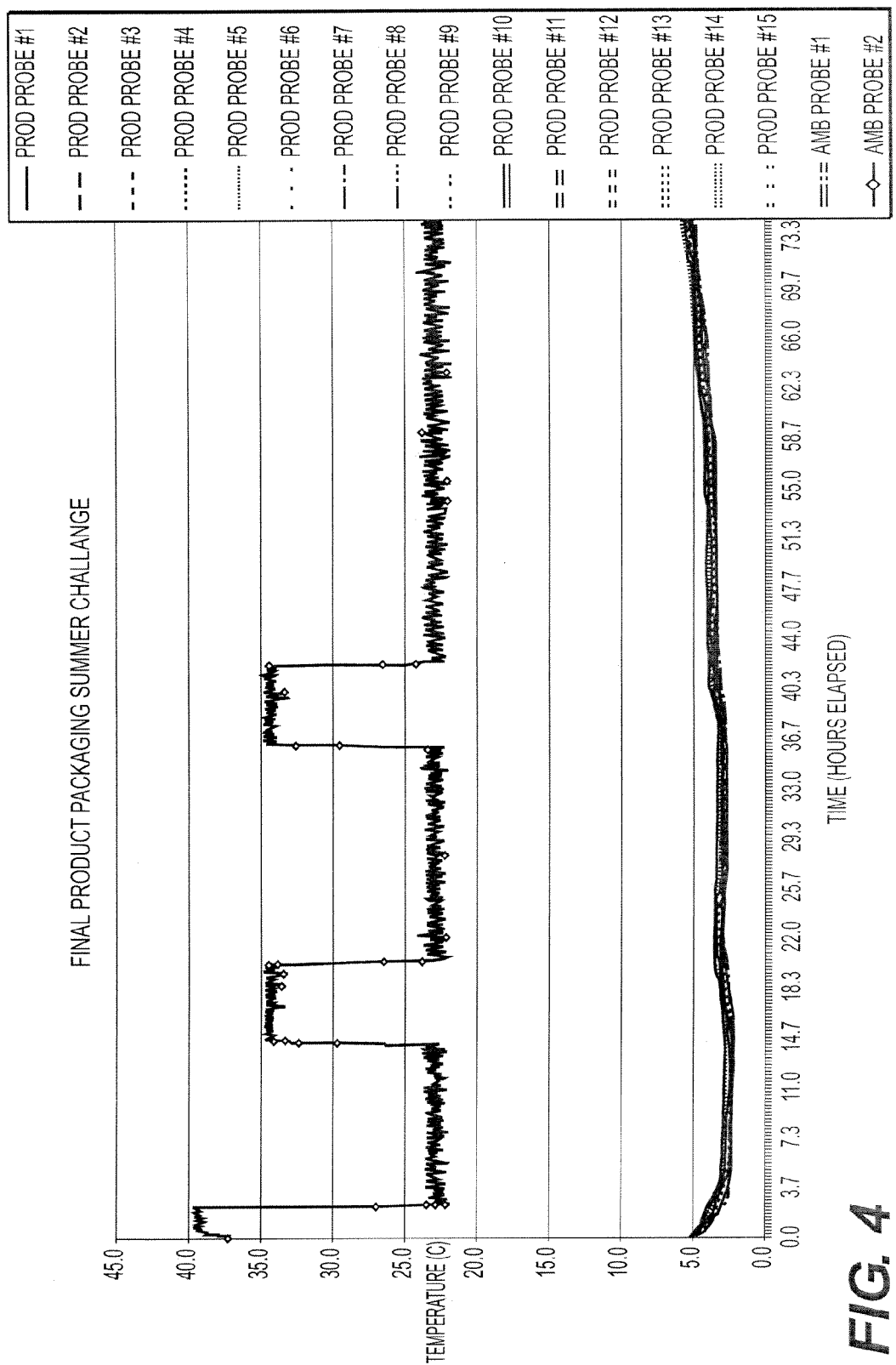
FIG. 4 is a graph showing a transport container system challenge for a hot summer, according to an exemplary embodiment.

To test the transport container system 10, a product efficacy assay can preferably be developed to determine the cell-based product's viability, cell yield, and dosage. Temperature profiles may also be developed for each individual product shelf life, and shipping method. For instance, the temperature of a shipped product and the environmental temperature (i.e., the temperature outside of the transport container system 10) can be plotted over time. As shown in FIG. 4, a simulated hot shipping profile can preferably be prepared based upon the average high temperatures and standard room temperature for a given region covering the projected delivery route for the hottest month of the year. The profile may incorporate two temperature spikes that simulate a non-temperature controlled shipping method, and two controlled ambient temperature storages, where each temperature spike can incorporate reasonable worst case temperatures for that region. Actual meteorological data can preferably be used to develop a realistic profile. The shipped product may be a cell-based product or a temperature sensor.

Figure 5:
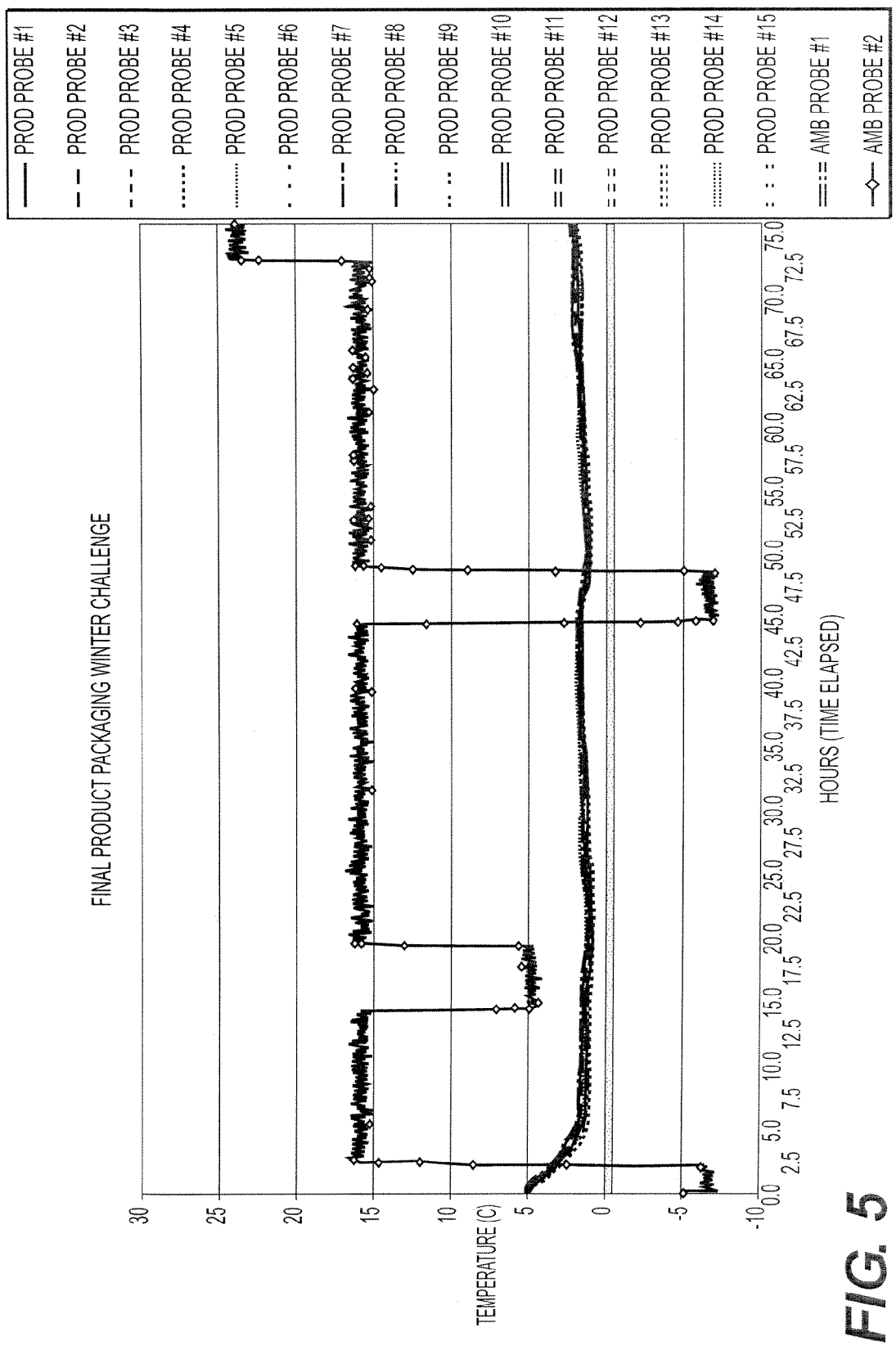
FIG. 5 is a graph showing a transport container system challenge for a cold winter, according to an exemplary embodiment.

Likewise, a cold temperature profile can also be developed. Using similar temperature data, a cold shipping profile such as the one shown in FIG. 5 can be developed based upon the average lows of a region covering the shipping route for the coldest month of the year. Safety factors can be added into each temperature spike to assure that each profile represents a worst case scenario shipping. Each successful package would be tested against both hot and cold shipping profiles and maintain the requirements for each worst case scenario. As previously discussed, the temperature of the product as well as the ambient environment may be measured, then the acceptance criteria determined based on results from the cell-based product's viability assay. Finally, the test may be repeated (e.g., in triplicate) to demonstrate reproducibility.

Example

The final product to be administered to patients in this study comprised autologous cultured skeletal myoblast cells (SMC) suspended in a delivery medium for injection. The suspension medium was Dulbecco's Modified Eagle's Medium (DMEM), with high glucose containing L-glutamine and HEPES buffer, without sodium pyruvate or Phenol Red, and containing Human Serum Albumin (HSA) at a concentration of 0.1%.

The final product packaging included one 7.5 mL crimped glass vial. The vial had undergone a container closure validation and all crimps were inspected prior to packaging. An International Air Transportation Association (IATA) transport container system (box 20 and canister 70) was qualified to maintain a temperature between −1° C. and 6° C. when challenged at extreme cold or hot external conditions (see FIGS. 4 and 5). This transport container system 10 was functionally tested with cells and temperature trackers and did not deviate outside of the −1° C. to 6° C. temperature range for at least 72 hours. This shipping temperature allowed for a stable product and increased the flexibility of the timeline for injection of the final product once shipped from the manufacturing site.

Preparation of the Skeletal Myoblast Cell (SMC) Product

Figure 6:
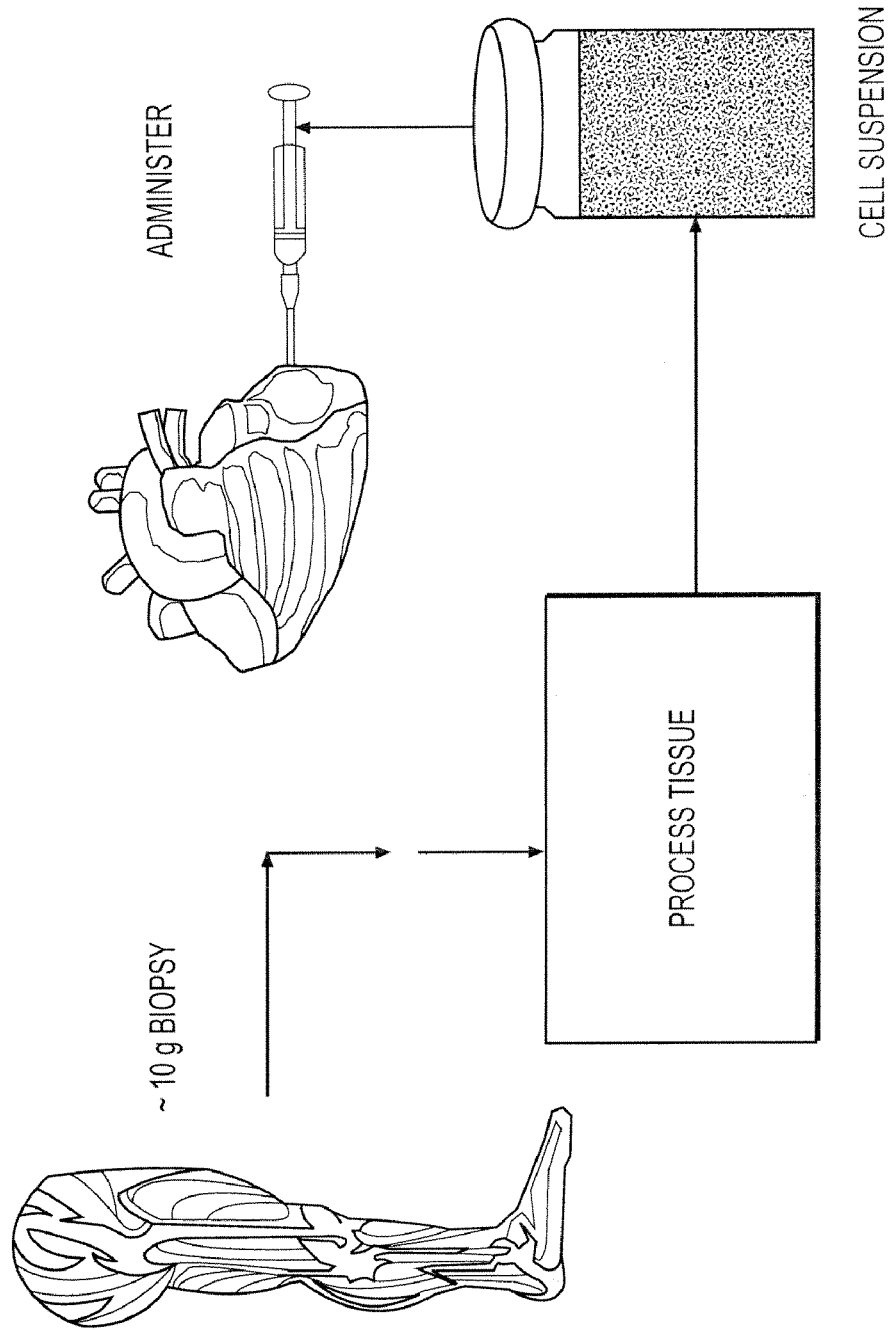
FIG. 6 is a flow diagram showing a general model for preparing an autologous cultured skeletal myoblast cell product, according to an exemplary embodiment.

Biopsy samples were collected from patients by surgical removal of approximately 10 grams of skeletal muscle tissue harvested from the vastus laterais muscle located in the upper leg, and cell cultures prepared from the biopsied tissue. Autologous skeletal myoblast cells were then prepared for the final product harvest upon confirmation of the surgery date by the clinical site. After cell processing, a cell suspension containing the skeletal myoblast cells was obtained. This suspension was then ready for storage, shipping and ultimately, administration by injection into a patient. A model of the preparation method is generally depicted in FIG. 6.

The Transport Container System

Each dose of autologous SMC was supplied in one sterile glass vial with a siliconized stopper and a flipoff-tearoff crimp. The final product vials were certified as USP Type I and European Pharmacopeia (EP) Type I specifications. The vials, stopper and crimp were sterilized prior to use. The stoppers were tested and found to have met USP biological reactivity requirements and physicochemical test for elastomeric closures for injections and the chemical and physical requirements for EP Type I stoppers. After assembly, the approved inspection vial was labeled with provided lot specific information. The labeled product vial was then placed into a 50 mL tube containing cushioning material and subsequently packed into a sealable transport canister 70. The canister 70 had a 1-inch foam insert 80 on the top and bottom. The canister 70 was labeled with lot specific information corresponding with the label information on the vial.

After receipt of the packaged and sealed canister 70, the canister 70 is placed into a shipping container 20. The shipping container 20 consisted of a foam insulated cardboard shipper, nine refrigerant packs 34 previously cooled to between 2° C. and 8° C., six frozen packs 36 previously frozen to −20° C. and a foam plug insert 110 on top. The shipping container 20 was configured to maintain a temperature range of −1° C. to 6° C. for at least 72 hours. On top of the sealed container 20 were final product instructions and a tracking/destruction record. The shipping container 20 was then fully labeled and placed in quarantine until ready for release.

Final Product Stability Studies

This shipping study involved clinical centers in San Francisco, Calif. and Cambridge, Mass. The shipping media, shipping temperature and shipping containers were validated to allow a shelf life for at least 72 hours. Final product shipping studies were conducted at a concentration of about $1.33 \times 10^8$ cells/mL and at the full shipping volume of 6.6 mL. The sealed vials 40 containing the final product cells 50 were placed into the transport container system 10 as described, and air transported to San Francisco, Calif. and back to Cambridge, Mass. The cells were held in the transport container system 10 for 72 hours. After 72 hours had elapsed, the vials 40 were retrieved from the container 20 and the cells were tested for viability, sterility, ability to proliferate, and formation of myotubes after the shipping and sterility results. The results from the study are summarized in Table 1 below.

TABLE 1

Results from Dynamic Shipping Stability Study

| Donor | Donor 1 | | Donor 2 | | Donor 3 | |
| --- | --- | --- | --- | --- | --- | --- |
| Time point | 0 Hours | 72 Hours | 0 Hours | 72 Hours | 0 Hours | 72 Hours |
| Sterility | No Growth | No Growth | No Growth | No Growth | No Growth | No Growth |
| Viability | 98.95 | 97.83 | 99.13 | 98.34 | 95.7 | 95.4 |
| Population Doublings | 0.806 | 0.808 | 0.802 | 0.886 | 0.931 | 0.967 |
| Myotube formation | Positive | Positive | Positive | Positive | Positive | Positive |

Figure 7:
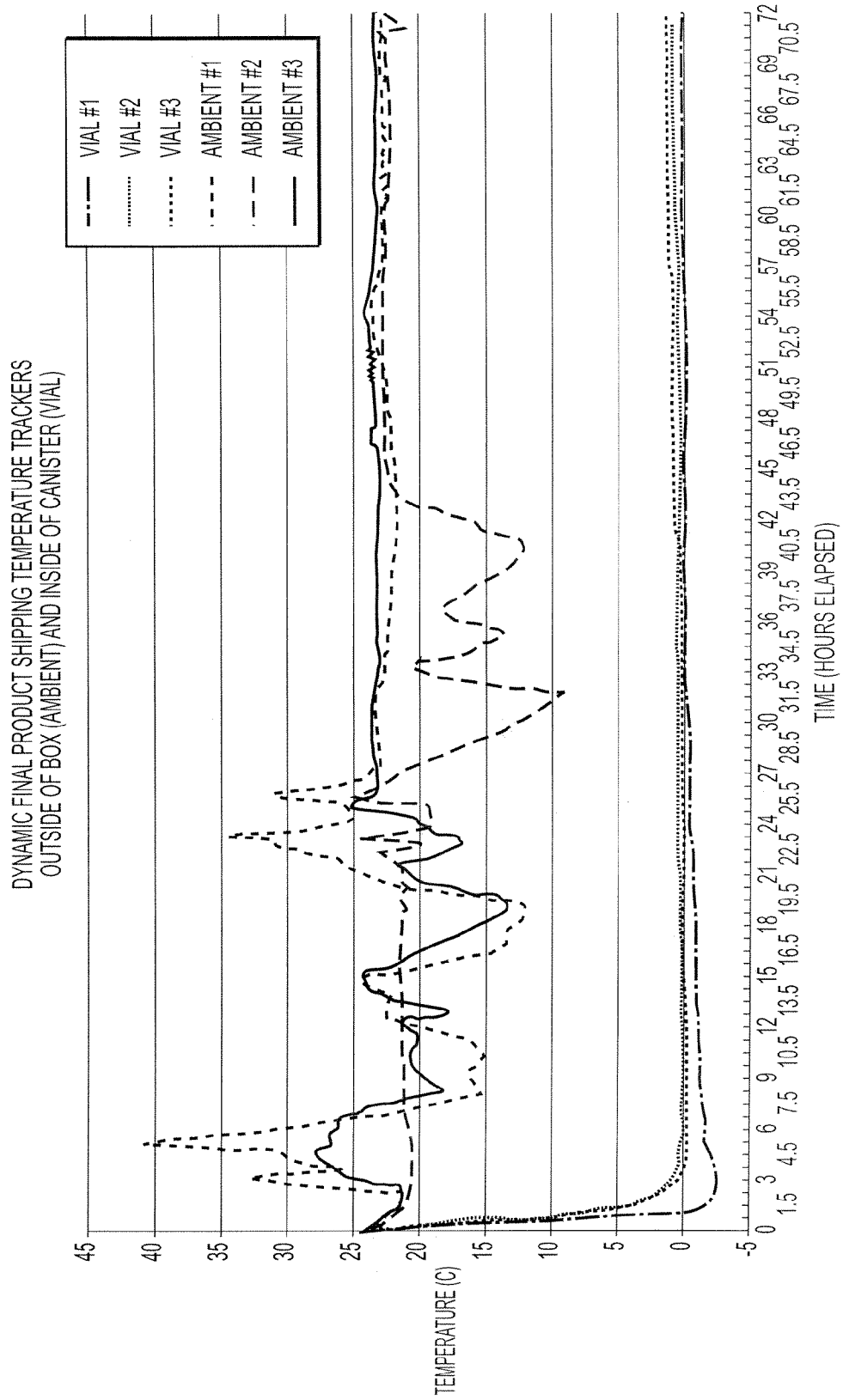
FIG. 7 is a graph tracking external and internal temperatures of a transport container system of an exemplary embodiment, during shipping.

Further, a check on the internal and external temperature of the transport container system 10 was taken using temperature probes such as, for example, COX TRACERS® sold by Cox Technologies, Inc. of Belmont, N.C. The results are shown in the graph of FIG. 7.

Other embodiments of the invention may be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A thermally insulated transport container system, comprising:
    a closable container having a thermally insulated portion, the container being configured for storage or shipment of a skeletal myoblast cell-based product;
    a sealable canister within the container, the canister being configured for holding the skeletal myoblast cell-based product; and
    a refrigerant within the container, the refrigerant being configured to maintain an internal temperature in the canister in the range of −5° C. to 15° C. for a period of at least 72 hours.

2. The system of claim 1, wherein the refrigerant is configured to maintain an internal temperature of the canister in the range of −1° C. to 10° C. for a period of at least 72 hours.

3. The system of claim 1, wherein the refrigerant is configured to maintain an internal temperature of the canister in the range of −1° C. to 6° C. for a period of at least 72 hours.

4. The system of claim 1, wherein the refrigerant is configured to maintain the internal temperature of the canister for a period of at least 96 hours.

5. The system of claim 1, wherein the refrigerant comprises a plurality of cold packs.

6. The system of claim 5, wherein the cold packs comprise silicate gel packs.

7. The system of claim 5, wherein some of the plurality of cold packs are a different temperature than a remainder of the cold packs.

8. The system of claim 7, wherein the plurality of cold packs comprise frozen and refrigerated packs.

9. The system of claim 7, wherein the plurality of cold packs are arranged in multiple layers around the sealed canister.

10. The system of claim 9, wherein the cold packs having a relative lower temperature are located on an outside layer.

11. The system of claim 10, wherein the cold packs having a relatively higher temperature are located on an inside layer.

12. The system of claim 1, wherein the skeletal myoblast cell-based product comprises cultured cells in suspension medium or shipping medium.

13. The system of claim 12, wherein the cultured cells comprise autologous cultured skeletal myoblast cells or allogeneic cultured skeletal myoblast cells.

14. The system of claim 12, wherein the suspension medium comprises Dulbecco's Modified Eagle's Medium.

15. The system of claim 14, wherein the medium further includes a protein stabilizer.

16. The system of claim 15, wherein the protein stabilizer is selected from the group consisting of human serum albumin and bovine serum albumin.

17. The system of claim 1, wherein cell viability is greater than 50% after 72 hours.

18. The system of claim 17, wherein cell viability is greater than 70% after 72 hours.

19. The system of claim 18, wherein cell viability is greater than 80% after 72 hours.

20. The system of claim 19, wherein cell viability is greater than 90% after 72 hours.

21. The system of claim 1, wherein the thermally insulated portion comprises blown polyurethane or styrofoam.

22. The system of claim 1, wherein the sealable canister further comprises at least one cushion insert.

23. The system of claim 22, wherein the at least one cushion insert is formed of a foam material.

24. A method of shipping cultured cells for transplantation, comprising:
    providing a closable container having a thermally insulated portion, the container being configured for storage or shipment of a skeletal myoblast cell-based product;
    providing a skeletal myoblast cell-based product in a sealed canister configured for holding cell-based products;
    placing the sealed canister into the container;
    providing a refrigerant for the container, the refrigerant being configured to maintain an internal temperature of the canister in the range of −5° C. to 15° C. for a period of at least 72 hours; and
    closing the container.

25. The method of claim 24, further including the step of arranging the refrigerant around the sealed canister prior to closing the container.

26. The method of claim 25, wherein the refrigerant comprises cold packs, and further wherein the step of arranging comprises placing a plurality of cold packs around the sealed canister.

27. The method of claim 26, wherein the step of placing comprises arranging multiple layers of cold packs around the sealed canister.

28. The method of claim 27, wherein the plurality of cold packs comprise refrigerated and frozen cold packs, and the step of arranging multiple layers comprise placing a layer of refrigerated cold packs around the sealed canister.

29. The method of claim 28, further including the step of placing a plurality of frozen cold packs around the refrigerated cold packs.

30. The method of claim 28, wherein the layer of refrigerated cold packs is placed adjacent to the sealed canister.

31. The method of claim 30, further including the step of providing two frozen and one refrigerated cold pack on top of the refrigerated cold packs.

32. The method of claim 31, wherein the refrigerated cold pack is positioned between the frozen cold packs.

33. The method of claim 24, wherein the cultured cells are contained in a glass vial and further including the step of providing cushion inserts within the sealed canister for cushioning the glass vial.

34. The method of claim 24, wherein the refrigerant is configured to maintain an internal temperature of the canister in the range of −1° C. to 10° C. for a period of at least 72 hours when the container has been closed.

35. The method of claim 24, wherein the refrigerant is configured to maintain an internal temperature of the canister in the range of −1° C. to 6° C. for a period of at least 72 hours when the container has been closed.

36. The method of claim 24, wherein the skeletal myoblast cell-based product comprises cultured cells in suspension medium or shipping medium.

37. The method of claim 36, wherein the cultured cells comprise autologous cultured skeletal myoblast cells or allogeneic cultured skeletal myoblast cells.

38. A method of transporting cell-based therapy products to a recipient, comprising:
    maintaining a cell-based therapy product at a temperature range of −1° C. to 6° C. during transportation for a duration of at least 48 hours, the cell-based therapy product being suspended in medium and configured for transplantation, and
    delivering the cell-based therapy product to the recipient in therapeutically acceptable condition.

39. The method of claim 38, wherein the cell-based therapy product comprises skeletal myoblast cells.

40. The method of claim 38, wherein the product is maintained at the temperature range for a duration of at least 72 hours.

41. The method of claim 38, wherein the product is maintained at the temperature range for a duration of at least 96 hours.

42. The method of claim 39, wherein the skeletal myoblast cells are maintained at a temperature range of 0° C. to 3° C. for a duration of at least 48 hours.

43. The method of claim 42, wherein the cells are maintained at the temperature range for a duration of at least 72 hours.

44. The method of claim 39, wherein cell viability of the delivered cells is greater than 90% at time of delivery to the recipient.

45. The method of claim 39, wherein proliferation doubling capacity of the delivered cells is at least 80% compared to non-shipped skeletal myoblast cells.

46. The method of claim 39, wherein the delivered cells are capable of forming myotubes.

47. The method of claim 39, further comprising the step of providing a thermally insulated transport container system for transporting the skeletal myoblast cells, the system comprising:
    a closable container having a thermally insulated portion, the container being configured for storage or shipment of the cell-based therapy product, a sealable canister within the container, the canister being configured for holding the skeletal myoblast cells, and a refrigerant within the container, the refrigerant being configured to maintain an internal temperature in the canister in the range of −1° C. to 6° C. for a period of at least 72 hours when the container has been closed.

48. A method for validating temperature stability during a shipping cycle for a closed container shipping system containing an item for delivery comprising:
    determining a duration of time for shipment of the item to a recipient;
    determining a desired temperature range for the item to be delivered;
    preparing a hot temperature shipping profile for the item to be delivered, the hot temperature shipping profile spanning at least the determined duration of time;
    preparing a cold temperature profile for the item to be delivered, the cold temperature profile spanning at least the determined duration of time;
    maintaining the item to be delivered under conditions simulating the environmental temperatures of the hot temperature shipping profile or the cold temperature shipping profile for at least the determined duration of time; and
    comparing the temperatures of the hot temperature shipping profile or cold temperature shipping profile to the desired temperature range.

49. The method of claim 48, further comprising the step of determining a shipping route for the delivery of the item.

50. The method of claim 49, wherein each temperature shipping profile comprises average temperatures and standard room temperatures for a geographic region covering the shipping route.

51. The method of claim 50, wherein each temperature shipping profile comprises actual meteorological data for the geographic region covering the shipping route.

52. The method of claim 50, wherein the hot temperature shipping profile comprises average temperatures and standard room temperatures for the average hottest month of the year for that geographic region.

53. The method of claim 50, wherein the cold temperature shipping profile comprises average temperatures and standard room temperatures for the average coldest month of the year for that geographic region.

54. The method of claim 48, wherein the item to be delivered comprises a temperature sensor.

55. The method of claim 48, wherein the item is a cell-based therapy product.

56. The method of claim 55, further including the step of determining the viability of the product after shipment.

\* \* \* \* \*